(12) United States Patent
Pav

(10) Patent No.: US 8,160,668 B2
(45) Date of Patent: Apr. 17, 2012

(54) PATHOLOGICAL CONDITION DETECTOR USING KERNEL METHODS AND OXIMETERS

(75) Inventor: Steven E. Pav, San Francisco, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1601 days.

(21) Appl. No.: 11/529,939

(22) Filed: Sep. 29, 2006

(65) Prior Publication Data

US 2008/0081974 A1  Apr. 3, 2008

(51) Int. Cl.
*A61B 5/1455* (2006.01)
*A61B 5/00* (2006.01)

(52) U.S. Cl. .................. 600/323; 600/300; 600/324

(58) Field of Classification Search ............ 600/323, 600/324, 336, 310, 322, 331, 300
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |
| 4,805,623 A | 2/1989 | Jöbsis |
| 4,911,167 A | 3/1990 | Corenman et al. |
| 4,936,679 A | 6/1990 | Mersch |
| 4,951,680 A * | 8/1990 | Kirk et al. ................ 600/511 |
| 4,972,331 A | 11/1990 | Chance |
| 5,119,815 A | 6/1992 | Chance |
| 5,122,974 A | 6/1992 | Chance |
| 5,167,230 A | 12/1992 | Chance |
| 5,297,548 A | 3/1994 | Pologe |
| 5,355,880 A | 10/1994 | Thomas et al. |
| 5,372,136 A | 12/1994 | Steuer et al. |
| 5,385,143 A | 1/1995 | Aoyagi |
| 5,398,682 A | 3/1995 | Lynn |
| 5,482,036 A | 1/1996 | Diab et al. |
| 5,505,199 A * | 4/1996 | Kim .............................. 600/323 |
| 5,553,614 A | 9/1996 | Chance |
| 5,564,417 A | 10/1996 | Chance |
| 5,575,285 A | 11/1996 | Takanashi et al. |
| 5,605,101 A | 2/1997 | Lynn |
| 5,630,413 A | 5/1997 | Thomas et al. |
| 5,645,059 A | 7/1997 | Fein et al. |
| 5,645,060 A | 7/1997 | Yorkey |
| 5,692,503 A | 12/1997 | Keunstner |
| 5,758,644 A | 6/1998 | Diab et al. |

(Continued)

FOREIGN PATENT DOCUMENTS

DE  102 13 692 A1  10/2003

(Continued)

OTHER PUBLICATIONS

Georgoulas et al., "Classification of Fetal Heart Rate using Scale Dependent Features and Support Vector Machines" 16th IFAC World Congress, Jul. 4-8, 2005, Prague Czech Republic.*

(Continued)

*Primary Examiner* — Eric Winakur
*Assistant Examiner* — Chu Chuan (JJ) Liu

(57) ABSTRACT

A method of manufacturing a pulse oximeter configured to classify patient data is disclosed. The method includes collecting a set of sample data and classifying the sample data as either pathological or normal using human expertise. The method also includes generating statistics representative of the saturation traces. A linear discriminator is composed having a non-linear transform that accepts the statistics as input and a pulse oximeter is programmed to compute the linear discriminator using a kernel function.

31 Claims, 6 Drawing Sheets

U.S. PATENT DOCUMENTS

| | | |
|---|---|---|
| 5,779,631 A | 7/1998 | Chance |
| 5,819,007 A | 10/1998 | Elghazzawi |
| 5,827,195 A | 10/1998 | Lander |
| 5,830,139 A | 11/1998 | Abreu |
| 5,842,981 A | 12/1998 | Larsen et al. |
| 5,873,821 A | 2/1999 | Chance et al. |
| 5,891,023 A | 4/1999 | Lynn |
| 5,924,980 A | 7/1999 | Coetzee |
| 5,938,594 A | 8/1999 | Poon et al. |
| 5,995,856 A | 11/1999 | Mannheimer et al. |
| 6,011,986 A | 1/2000 | Diab et al. |
| 6,047,201 A * | 4/2000 | Jackson, III ............ 600/323 |
| 6,064,898 A | 5/2000 | Aldrich |
| 6,120,460 A | 9/2000 | Abreu |
| 6,134,460 A | 10/2000 | Chance |
| 6,135,952 A | 10/2000 | Coetzee |
| 6,163,715 A | 12/2000 | Larsen et al. |
| 6,181,958 B1 | 1/2001 | Steuer et al. |
| 6,223,064 B1 | 4/2001 | Lynn et al. |
| 6,230,035 B1 | 5/2001 | Aoyagi et al. |
| 6,246,892 B1 | 6/2001 | Chance |
| 6,266,546 B1 | 7/2001 | Steuer et al. |
| 6,312,393 B1 | 11/2001 | Abreu |
| 6,342,039 B1 | 1/2002 | Lynn et al. |
| 6,397,091 B2 | 5/2002 | Diab et al. |
| 6,415,236 B2 | 7/2002 | Kobayashi et al. |
| 6,438,399 B1 | 8/2002 | Kurth |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,591,122 B2 | 7/2003 | Schmitt |
| 6,594,513 B1 | 7/2003 | Jobsis et al. |
| 6,606,509 B2 | 8/2003 | Schmitt |
| 6,608,934 B2 | 8/2003 | Scheirer |
| 6,609,016 B1 | 8/2003 | Lynn |
| 6,615,064 B1 | 9/2003 | Aldrich |
| 6,622,095 B2 | 9/2003 | Kobayashi et al. |
| 6,658,277 B2 | 12/2003 | Wasserman |
| 6,662,030 B2 | 12/2003 | Khalil et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,690,958 B1 | 2/2004 | Walker et al. |
| 6,708,048 B1 | 3/2004 | Chance |
| 6,711,424 B1 | 3/2004 | Fine et al. |
| 6,711,425 B1 | 3/2004 | Reuss |
| 6,748,252 B2 | 6/2004 | Lynn et al. |
| 6,760,608 B2 | 7/2004 | Lynn |
| 6,785,568 B2 | 8/2004 | Chance |
| 6,801,797 B2 | 10/2004 | Mannheimer et al. |
| 6,801,799 B2 | 10/2004 | Mendelson |
| 6,811,538 B2 | 11/2004 | Westbrook et al. |
| 6,839,581 B1 * | 1/2005 | El-Solh et al. .............. 600/323 |
| 6,873,865 B2 | 3/2005 | Steuer et al. |
| 6,931,269 B2 * | 8/2005 | Terry ............................ 600/323 |
| 6,949,081 B1 | 9/2005 | Chance |
| 6,961,598 B2 | 11/2005 | Diab |
| 7,025,729 B2 | 4/2006 | De Chazal et al. |
| 7,027,849 B2 | 4/2006 | Al-Ali |
| 7,027,850 B2 | 4/2006 | Wasserman |
| 7,031,857 B2 | 4/2006 | Tarassenko et al. |
| 7,060,035 B2 | 6/2006 | Wasserman |
| 7,079,888 B2 | 7/2006 | Oung |
| 7,081,095 B2 | 7/2006 | Lynn et al. |
| 7,225,013 B2 | 5/2007 | Geva et al. |
| 7,268,873 B2 | 9/2007 | Sevick-Muraca et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0161287 A1 | 10/2002 | Schmitt |
| 2002/0161290 A1 | 10/2002 | Chance |
| 2002/0165439 A1 | 11/2002 | Schmitt |
| 2002/0190863 A1 | 12/2002 | Lynn et al. |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0078504 A1 * | 4/2003 | Rowe ............................ 600/476 |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0024298 A1 * | 2/2004 | Marshik-Geurts et al. ... 600/326 |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0080323 A1 | 4/2005 | Kato |
| 2005/0101850 A1 | 5/2005 | Parker |
| 2005/0107676 A1 | 5/2005 | Acosta et al. |
| 2005/0113656 A1 | 5/2005 | Chance |
| 2005/0113703 A1 * | 5/2005 | Farringdon et al. ........... 600/509 |
| 2005/0168722 A1 | 8/2005 | Forstner et al. |
| 2005/0192488 A1 | 9/2005 | Bryenton et al. |
| 2005/0203357 A1 | 9/2005 | Debreczeny et al. |
| 2005/0267346 A1 | 12/2005 | Faber et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0149144 A1 | 7/2006 | Lynn |
| 2006/0155589 A1 | 7/2006 | Lane et al. |
| 2006/0247532 A1 * | 11/2006 | Ramanujam et al. ......... 600/476 |
| 2007/0167694 A1 | 7/2007 | Causevic et al. |
| 2008/0269583 A1 | 10/2008 | Reisfeld |

FOREIGN PATENT DOCUMENTS

| | | |
|---|---|---|
| JP | 5-212016 | 8/1993 |
| WO | WO 92/20273 | 11/1992 |
| WO | WO 94/03102 | 2/1994 |
| WO | WO 97/49330 | 12/1997 |
| WO | WO 01/45553 A1 | 6/2001 |
| WO | 2005087097 A | 9/2005 |
| WO | WO 2005/087097 A | 9/2005 |

OTHER PUBLICATIONS

Burges, "A Tutorial on Support Vector Machines for Pattern Recognition", Data Mining and Knowledge Discovery, vol. 2, Issue 2, pp. 121-167, Jun. 1998.*

Cho S P et al: "Detection of Arousals in Patients with Respiratory Sleep Disorders Using a Single Channel EEG" Engineering in Medicine and Biology Society, 2005, IEEE-EMBS 2005. 27th Annual International Conference of the Shanghai, China Sep. 1-4, 2005, Piscataway, NJ, USA, IEEE, Sep. 1, 2005, pp. 2733-2735, XP010908367 ISBN: 0-7803-8741-4 the whole document.

Kirby S D et al: "Neural network prediction of obstructive sleep apnea from clinical criteria." CHEST Aug. 1999, vol. 116, No. 2, pp. 409-415, XP002464334, ISSN: 0012-3692 the whole document.

Semienchuk S M et al: "A Portable, PC-Based Monitor for Automated, On-line Cardiorespiratory State Classification" Engineering in Medicine and Biology Society, 2005. IEEE-EMBS 2005. 27th Annual International Conference of the Shanghai, China Sep. 1-4, 2005, Piscataway, NJ, USA, IEEE, Sep. 1, 2005, pp. 4420-4423, XP010906764, ISBN: 0-7803-8741-4 the whole document.

A. Bernhard Schölkoph and Alex Smola; "Kernal Methods and Support Vector Machines"; article URL citeseer.csail.mit.edu/688798.html; Feb. 27, 2003; pp. 1-5.

A. Smola and B. Schölkoph; "A Tutorial on Support Vector Regression"; Technical report, 1998. http://sml.nicta.com.au/Publications/homepublications/papers/2004/smoSch04.pdf; Sep. 30, 2003, pp. 1-14.

Pai-Hsuen Chen, Chih-Jen Lin and Bernhard Schölkoph; "A Tutorial on v-Support Vector Machines"; Applied Stochastic Models in Business and Industry, 21:111-136, 2005. URL www.csie.ntu.edu/tw/~cjlin/papers/nusvmtutorial.pdf; 29 pages.

Klaus-Robert Müller, Sebastian Mika, Gunnar Rätsch, Koji Tsuda and Bernhard Schölkopf; "An Introduction to Kernal-Based Learning Algorithms"; IEEE Transactions on Neutral Networks, 12(2);181-202, Mar. 2001; pp. 181-202.

Lee, Jason C.S., et al., "Measurement of Percent Carboxyhemoglobin with Pulse-Oximetry Technique," *IEEE Engineering in Medicine & Biology Society 10th Annual International Conference*, CH2566-88, vol. 88, pp. 1781-1782 (1988).

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093.

Bongard, Frederic S., et al., "Continuous Dual Oximetry in Surgical critical care—Indications and Limitations," *Annals of Surgery*, vol. 216, No. 1, pp. 60-68 (1992).

Kirby, S.D., et al.; "Neural network prediction of obstructive sleep apnea from clinical criteria," *Chest*, Aug. 1999, vol. 116, No. 2; pp. 409-415.

Cho, S.P., et al.; "Detection fo Arousals in Patients with Respiratory Sleep Disorders Using a single Channel EEG," *Engineering in Medicine and Biology Society*, 2005; *IEEE-EMBS 2005 27th annual International Conference*, Shanghai, China; Sep. 1-4, 2005; pp. 2733-2735.

Semienchuk, S.M., et al.; "A Portable, PC-Based Monitor for Automated, On-line Cardiorespiratory State Classification," *Engineering in Medicine and Biology Society*, 2005; *IEEE-EMBS 2005 27th Annual International Conference*, Shanghai, China (Sep. 1-4, 2005), pp. 4420-4423.

\* cited by examiner

PATHOLOGICAL CONDITION DETECTOR USING KERNEL METHODS AND OXIMETERS

BACKGROUND OF THE INVENTION

1. Field of the Invention

The present invention relates generally to medical devices and, more particularly, to sensors used for detecting physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics such as the blood oxygen saturation of hemoglobin in arterial blood, the volume of individual blood pulsations supplying the tissue and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a noninvasive sensor that transmits electromagnetic radiation, such as light, through a patient's tissue and that photoelectrically detects the absorption and scattering of the transmitted light in such tissue. One or more of the above physiological characteristics may then be calculated based upon the amount of light absorbed and scattered. More specifically, the light passed through the tissue is typically selected to be of one or more wavelengths that may be absorbed and scattered by the blood in an amount correlative to the amount of the blood constituent present in the tissue. The measured amount of light absorbed and scattered may then be used to estimate the amount of blood constituent in the tissue using various algorithms.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, a method of manufacturing a pulse oximeter configured to classify patient data is disclosed. The method includes collecting a set of sample data and classifying the sample data as either pathological or normal using human expertise. The method also includes generating statistics representative of the sample data. A linear discriminator is composed having a non-linear transform that accepts as input the statistics resulting from the statistical analysis and a pulse oximeter is programmed to compute the linear discriminator using a kernel function.

In accordance with another aspect of the present invention, a method for detecting a pathological condition is provided. The method includes obtaining percent oxygen saturation data from a patient using a pulse oximeter and classifying the percent oxygen saturation data using a kernel based classifier programmed into the pulse oximeter. The kernel based classifier is trained on sample data categorized by a trained expert. The kernel based classifier is configured to categorize the percent oxygen saturation data as indicating a normal state or a pathological state.

In accordance with yet another aspect of the present invention an oximeter system configured to detect a pathological condition is provided. The oximeter system includes a sensor unit configured to generate a signal representative of detected electromagnetic radiation that has been transmitted into blood perfused tissue. Additionally, the oximeter system includes an oximeter unit configured to determine percent saturation of hemoglobin data based on the signal. The oximeter unit is configured to classify the percent saturation of hemoglobin data as being normal or pathological according to a kernel based classifier. The kernel based classifier is trained using sample data that has been classified by a human expert and statistically analyzed.

BRIEF DESCRIPTION OF THE DRAWINGS

Certain exemplary embodiments are described in the following detailed description and in reference to the drawings, in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Pulse oximetry systems may be configured to display traces of the percent oxygen saturation of hemoglobin. By simply looking at the saturation traces, a trained expert, such as a physician, can quickly identify whether a patient is suffering from a pathological condition. For example, a trained physician may notice trends in the saturation traces indicative of respiratory distress caused by an apneaic event. However, while such an apneaic event may be obvious to a trained physician observing saturation traces, a trained physician is not always available to identify the saturation trace trends that may be indicative of a pathological condition.

Accordingly, a support vector machine (SVM) implementing a kernel to classify multidimensional points of data to detect pathological conditions is disclosed. Specifically, the kernel-based classifier scheme is disclosed to detect pathological conditions, such as airway instability, from the trace of oxygen saturation over time. The SVM may be trained on a set of calibration data which have been adjudged by an expert, such as a trained physician, to belong in one of two categories (e.g., normal and pathological). A statistical evaluation of the classified traces is performed to determine variables that may be used in the kernel. The kernel uses the variables in classifying a current saturation trace and outputs an indication as to whether the trace indicates a normal or pathological condition. The use of the kernel function allows classification to be performed after a nonlinear transform of the data, which is to say that discrete points do not need to be linearly separable. The system and method disclosed, therefore, provides for detection of a pathological condition by an oximetry system implementing the SVM. In the interest of clarity, examples of training a classifier are provided by way of discussion below and illustrated in the figures.

Expert Classification

Figure 1:
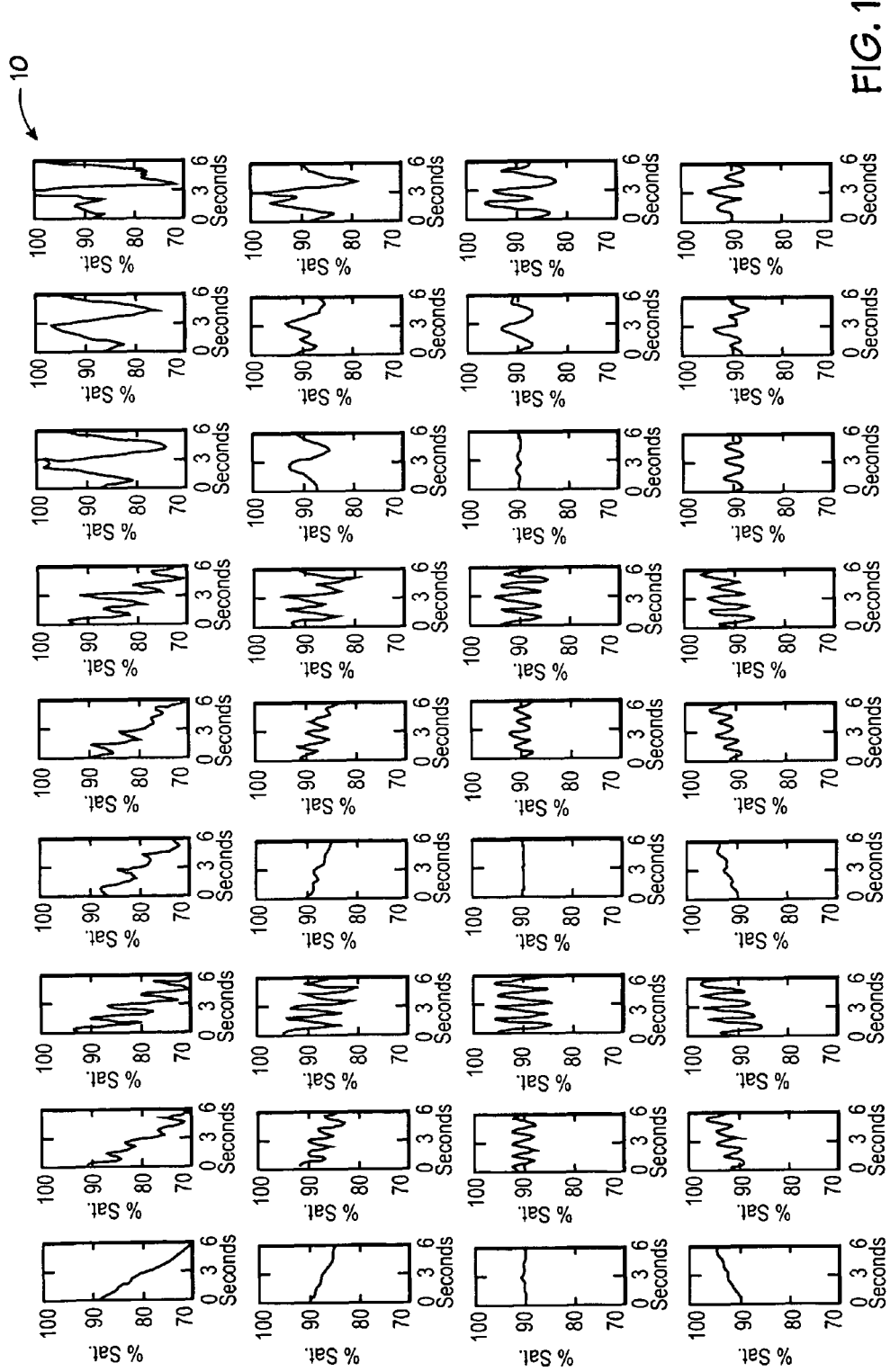
FIG. 1 is a set of simulated saturation traces in accordance with an exemplary embodiment of the present invention.

Referring to FIG. 1, a number of simulated saturation traces are shown in accordance with an exemplary embodiment of the present invention and are generally designated by the reference numeral 10. The horizontal axes of the traces 10 indicate time in seconds. Each saturation trace indicates the percent saturation over 6 seconds. In alternative embodiments, the saturation traces may have a longer or shorter duration. The vertical axes of the traces 10 indicate the percent saturation of oxygen in hemoglobin. Seemingly healthy individuals typically have a saturation level greater than 90% and saturation levels under 70% are typically indicative of a pathological condition in and of themselves. Therefore, only the range of saturation between 70%-100% saturation is included in the traces 10.

The saturation traces 10 illustrate various trends, regularities and irregularities which may be found in a random set of saturation traces from patients. Some of the traces illustrate a pathological condition, such as apnea, while other traces may indicate normal conditions of a healthy individual. A trained expert, such as a physician, may be capable of identifying saturation traces indicative of a pathological condition, such as a patient in respiratory distress. The saturation trace pattern is likely a symptom of an underlying condition, rather than a condition itself. Therefore, certain statistical features of the trace may be determined which might be associated with normal and pathological conditions, as adjudged by the trained expert. Given sufficient data, a learning algorithm can distinguish which statistics are important.

In accordance with an exemplary embodiment of the present invention, a two-dimensional classifying scheme is disclosed. The two-dimensional classifying scheme includes selecting two trace parameters that may be significant in categorizing traces as being indicative of a pathological condition. For example, slope and linearity may be selected if it is determined that they may be indicative of a pathological condition. Alternatively, other statistical parameters may be used that are determined to be indicative of a pathological condition. An infinite impulse response (IIR) least squares regression of saturation to the model $S_k=\hat{m}k+\hat{b}$, where $S_k$ is the saturation at time k can be performed. A tunable parameter in the IIR regression determines how much older observations are down weighted. The square of the Pearson's coefficient of the data, $r^2$, is computed within an IIR framework to indicate linearity of the data over time.

Figure 2:
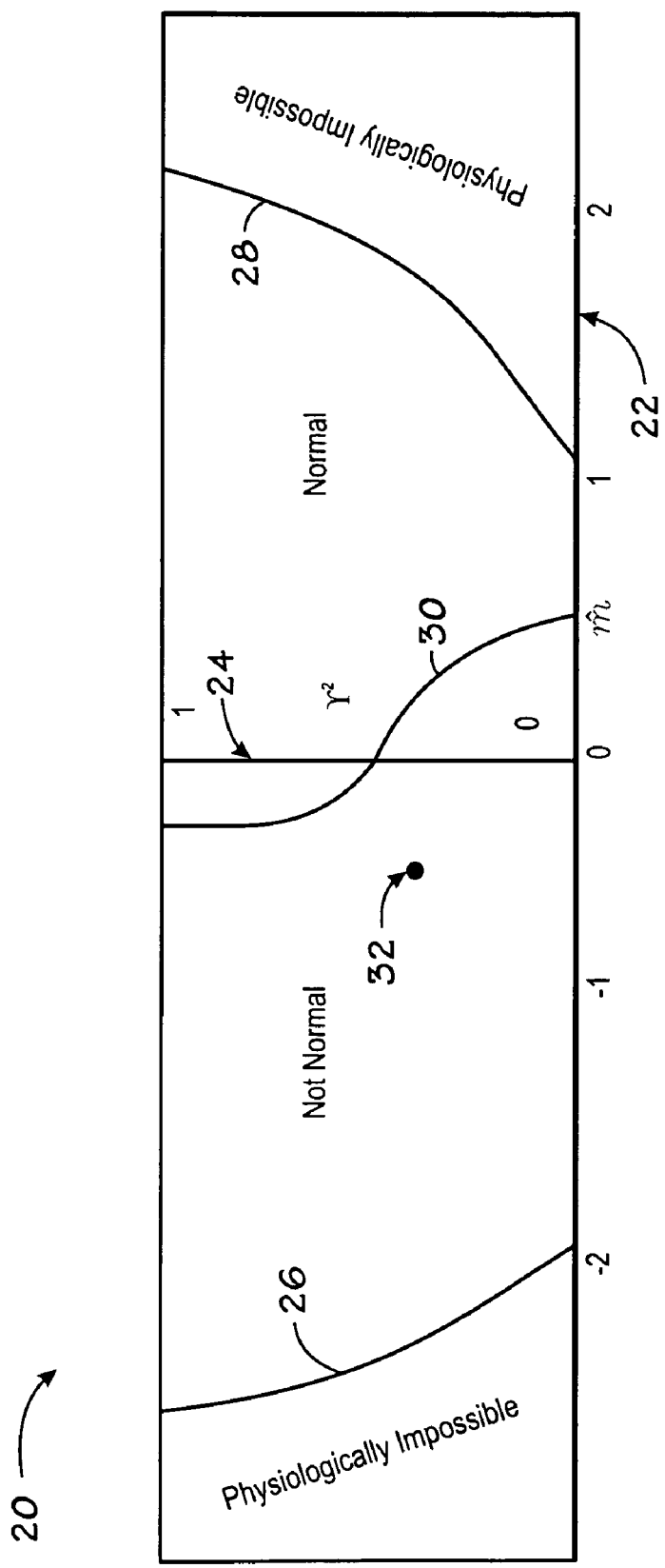
FIG. 2 illustrates a slope and linearity graph with defined regions in accordance with an exemplary embodiment of the present invention.

Turning to FIG. 2, a slope ($\hat{m}$) and linearity ($r^2$) graph 20 is shown in accordance with an exemplary embodiment of the present invention. The graph 20 is illustrative of a two dimensional classification scheme plotting the slope of a saturation trace against its linearity, with the slope being the horizontal axis 22 and linearity being the vertical axis 24. According to the trained expert's determinations, regions in the graph 20 may be categorized as "Normal" or "Pathological." Specifically, for example, the expert could classify the traces, such as those shown in FIG. 1. The classified traces may be plotted in a graph, such as the graph 20, and by which the expert might notice that the classified points are separable by a line. While the expert may be able to notice irregularities in traces, once more than two statistics are used, it is difficult to visualize the plots and thus separate the classified points. Thus, as will be discussed below, in dimensions greater than three, a computer learning technique is used to do the separations in high dimensions rather than the experts doing it directly.

The graph 20 also illustrates a "Physiologically Impossible" region which is represented by the area outside lines 26 and 28. The Physiologically Impossible region may be considered a physical impossibility region indicating death or that the sensor is no longer positioned to take accurate readings, such as if the sensor is no longer on the patient. Because of their physical impossibility status, such regions do not need to be classified by the expert and should not appear in data used to train the classifier. Furthermore, such regions are not included in the classification scheme programmed into the oximeter and, therefore, will not be discussed in greater detail.

In the graph 20, the line 30 separates regions where a trace is classified as Normal and where a trace is classified as Not Normal. The Normal region, generally located on the right side of the graph 20, may be an area where the slope and linearity of the trace has been adjudged to be acceptable and not indicative of an underlying problem. The Not Normal region, generally located on the left side of the graph 20, may be an area where the slope and linearity of the trace has been adjudged to indicate an underlying problem, such as a pathological condition.

Measured saturation traces may be indicated by a single point, such as point 32 based upon the statistical parameters of a trace, i.e., slope and linearity, as shown in FIG. 2. The point 32 lies within the Not Normal region, indicating that the trace it represents has slope and linearity features to indicate that the patient may be suffering from a pathological condition. For example, in the event that the two dimensional classifying scheme has been trained to classify traces for apneaic events, meaning that the line 30 has been generated as a discriminator between traces that indicate apnea and those that do not, it may indicate that the patient has apnea.

Figure 3:
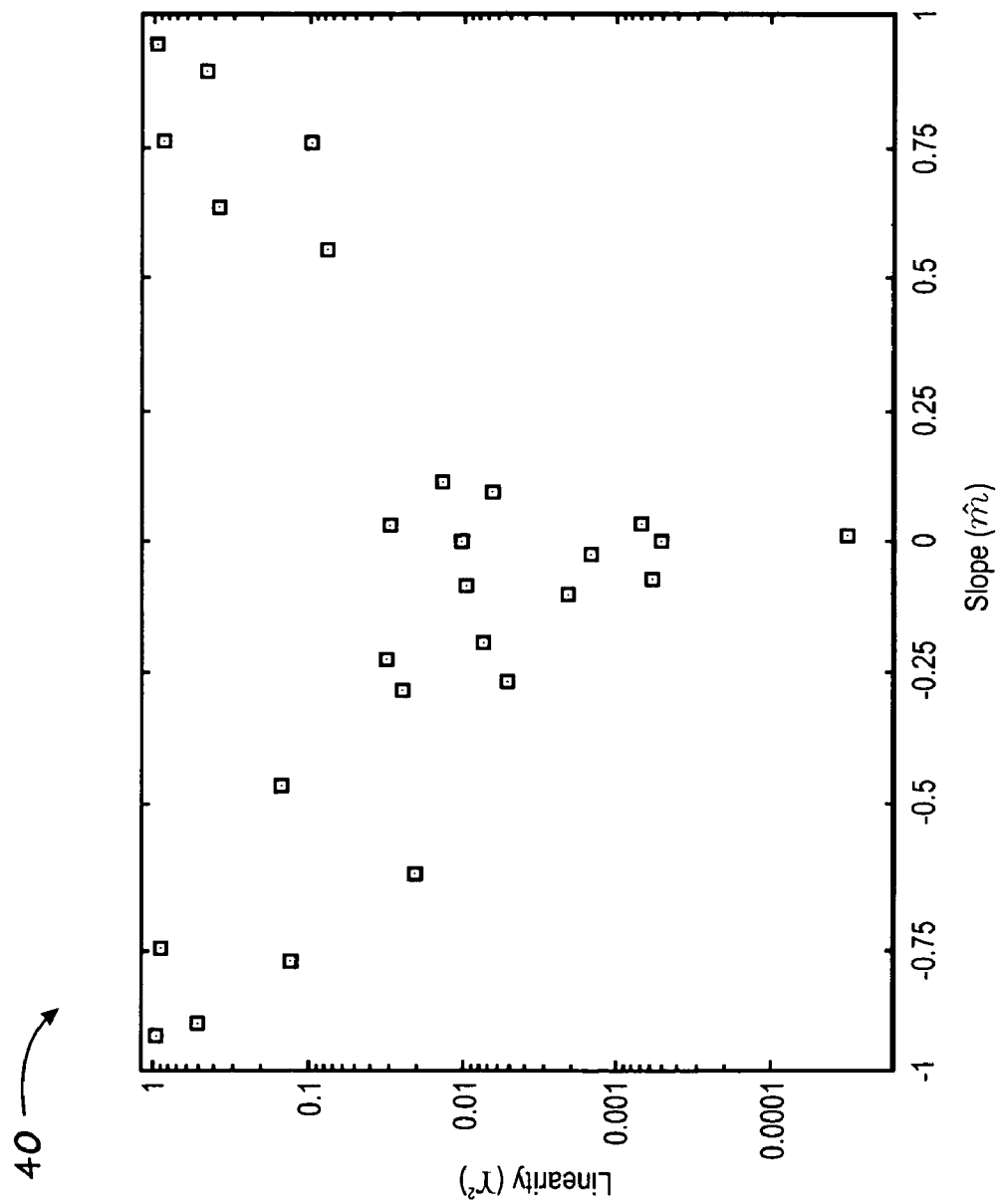
FIG. 3 illustrates a graph of the saturation traces from FIG. 1 in accordance with an exemplary embodiment of the present invention.

Referring to FIG. 3, a slope and linearity plot 40 of all of the saturation traces of FIG. 1 is illustrated in accordance with an exemplary embodiment of the present invention. Each trace of FIG. 1 is represented by a point in the plot 40. As can be seen, there are general groupings of points near the center, towards the upper right hand corner, and towards the upper left hand corner of the plot 40. The points in the upper right hand corner are indicative of traces having an upward sloping and a more linear trend. Contrastingly, points in the upper left hand corner are indicative of saturation traces having a downward slope and linear trend. The points near the middle of the plot 40 have little or no slope trend and have varying degrees of linearity. The line 30 which separated Normal and Not Normal regions in FIG. 2 may not be an appropriate or accurate delineator for this set of data. Indeed, the Normal and Not Normal regions may take entirely different shapes. Additionally, the slope and linearity parameters may not be sufficient to accurately define the Normal and Not Normal regions. As such, other statistical parameters may be useful. Once more than two statistical parameters are analyzed, however, it is no longer easy to plot the regions in space. Moreover, regions of interest cannot be determined from first principles, meaning the regions cannot be known a priori, or without actually computing the vectors that define the region.

Therefore, in accordance with an alternative exemplary embodiment, a kernel program that weighs statistically significant parameters and automatically categorizes the saturation traces as being indicative of a pathological condition or a normal condition is disclosed. Specifically, a kernel program can be created and trained to indicate pathological conditions, such as airway instability, apnea, and respiratory distress. Indeed, numerous pathological conditions which affect respiration and circulation in a time-varying manner may possibly be detected with this method. For example, applicable conditions may include chronic obstructive pulmonary disease(COPD), onset of pulmonary edema or pulmonary embolism, pulmonary hypertension, endomyocardial fibrosis, chronic rheumatic heart diseases, including valve disorders, and subendocardial infarctions. Depending on incidence and chances of early intervention, many of the conditions which possibly could be detected may not ever be sufficiently tested and trained, rather, received training data which includes saturation traces of patients with numerous worrisome conditions may be obtained, and an alarm may merely indicate "trouble" rather than the presence of a specific pathological condition, such as aortic valve malfunction. Therefore, there are at least two methods to train the classifier. First, the expert may look at the saturation traces and classify them as "the doctor should see this" or "the doctor need not see this." The SVM may then be trained with kernels to these classifications. The other method of training includes obtaining saturation traces from two populations, one with a pathological condition X, and one without the pathological condition X. The SVM may then be trained accordingly to indicate the presence of this specific pathological condition.

As mentioned above, the importance of a particular trend may depend on parameters besides the slope and linearity, such as the mean saturation state, e.g., a strong desaturation event from a mean of 99 may not be as distressing as one from a mean of 75. Additionally, other statistics which may be of interest include: the IIR sample variance, the difference between the mean of the positive first differences and the mean of the negative first differences as a rough measure of asymmetry of local trends, the frequency of the saturation with the highest energy using a Fourier transform, minimum saturation over the past 5, 30, 60 seconds, compressibility, or other such statistical parameters. The IIR sample variance and mean statistics, as well as higher order statistics, may also be considered over varying time scales. Essentially, any parameter that may aid in distinguishing between a normal and a pathological state may be included in the list. The importance of a particular statistic of interest can be determined by computing the statistic for saturation traces which have been classified to be in various states by a trained expert and an algorithmic classifier can then be trained on the data.

Support Vector Machines

A basic framework for support vector machines (SVMs) which determine discriminators used to classify data is set forth below. For a more detailed discussion, reference may be made to two articles by Alex Smola and Bernhard Scholkopf, *A Tutorial on Support Vector Regression*, STATISTICS AND COMPUTING, 14:199-222 (2004); and *Support Vector Machines and Kernel Algorithms*, ENCYCLOPEDIA OF BIOSTATISTICS, John Wiley and Sons (2003), which are incorporated herein by reference. In the following discussion, the various statistics of interest form the vectors $x_i$ while the presence or absence of a given condition, as judged by an expert, is denoted by $y_i$.

A set of calibration data $(x_1, y_1), (x_2, y_2), \ldots (x_n, y_n)$ is available with the $x_i$ vectors in l-dimensional space (hereafter denoted $\mathbb{R}^l$), and the $y_i$ are either +1 or −1 to denote, respectively, the presence or absence of some condition or the membership in one of two groups. The calibration data, such as the exemplary set of saturation traces of FIG. 1, are adjudged by an expert. As outline above, each $x_i$ is a vector of statistics which have been generated from the saturation traces classified as +1 or −1 by the human expert. As such, the $x_i$ are not classified by the experts. The discriminator is a function from $\mathbb{R}^l$ to the set (−1, +1). The most basic discriminator is the two-valued sign function $\mathbb{R}^l$:

$$\text{sign}(x) = \begin{cases} -1 \text{ if } x < 0 \\ 1 \text{ if } x \geq 0 \end{cases}. \tag{1}$$

The sign function is inherently ill-conditioned, so it is not important that it seems arbitrarily defined at x=0.

Figure 4:
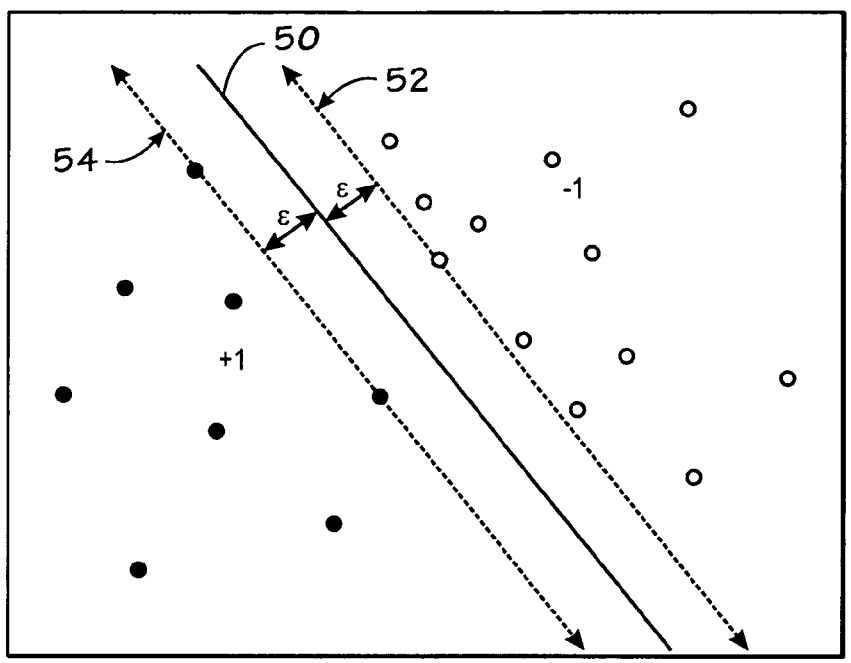
FIG. 4 illustrates a good discriminator line in accordance with an exemplary embodiment of the present invention.
Figure 5:
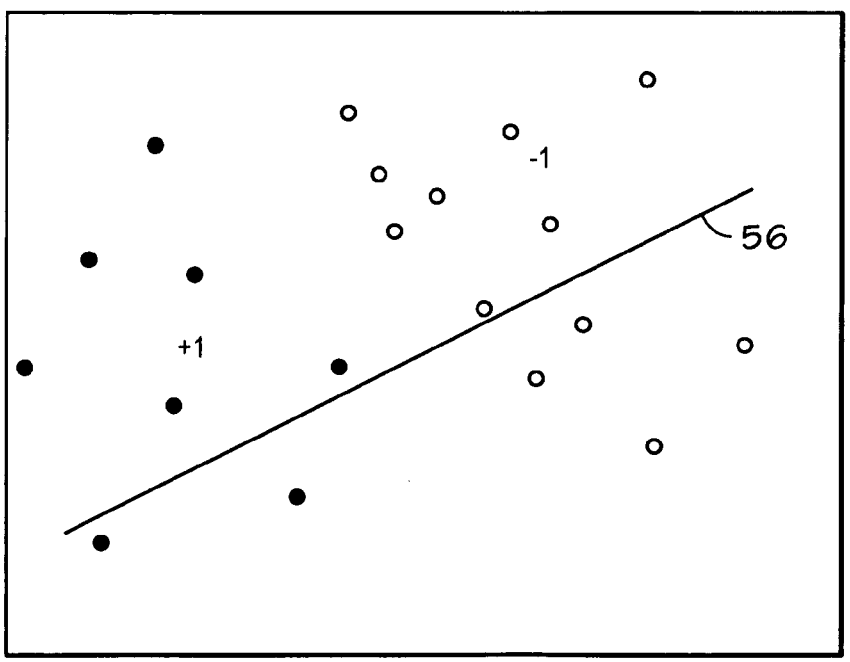
FIG. 5 illustrates a poor discriminator line in accordance with an exemplary embodiment of the present invention.

A linear discriminator, such as those shown in FIGS. 4 and 5, is a function of the form:

$$f(x) = \text{sign}(w^T x + b), \tag{2}$$

where w is an l-vector, and b is a scalar. A linear discriminator divides the data into two classes by a hyperplane. All points in a closed halfspace are assigned value 1, while those points in the complement are assigned value −1.

A linear discriminator 50 in $\mathbb{R}^2$ with some calibration data are shown in FIG. 4. The discriminator 50 is a line or hyperplane which accurately classifies the calibration data, unlike the poor discriminator 56 of FIG. 5. Note the presence of the margins 52 and 54, each of width $\epsilon$, in FIG. 4. The margins are defined as:

$$\epsilon = \min_{i} \frac{w^T x_i + b}{\|w\|^2} Y_i. \tag{3}$$

The margin is non-negative if and only if all the calibration data are accurately classified. The presence of a large margin decreases the likelihood of false negatives or positives and also diminishes the effect of ill-posedness, i.e., the arbitrary definition of sign (x) at x=0. For a given w, there is a unique b which maximizes the margin. Assuming that this b is always selected, the problem is reduced to finding the best w. Under this choice, the margin is dependent only on the direction of w, not its magnitude. Therefore, w can be assumed to be a unit-length vector.

To find an optimal classifier, the w and b that maximize the margin can be found by the equation:

$$\max_{w,b:\|w\|_2=1} \min_i \frac{w^T x_i + b}{\|w\|_2} y_i. \quad (4)$$

This optimization problem is difficult to deal with, however, as it has a minimization inside a maximization. To avoid this problem, the optimization may be re-written, given w and b, such that:

$$(w^t x_i + b) y_i \geq 1 \forall i. \quad (5)$$

It can then be shown that the margin is at least $1/\|w\|_2$ This leads to the constrained optimization form:

$$\min_{w,b:(w^T x_i + b) y_i \geq 1} \|w\|_2, \quad (6)$$

which has a solution equivalent to that of optimization problem (4). To maximize a positive $f(x)$, it suffices to maximize $f^2(x)$, thus, the preferable form:

$$\min_{w,b:(w^T x_i + b) y_i \geq 1} \|w\|_2^2 = w^T w, \quad (7)$$

may be achieved. Problem (7) is a quadratic programming problem for which there are a number of numerical approaches. One approach commonly used in support vector machines is that of "Sequential Minimal Optimization" as outlined by Pai-Hsuen Chen, Chih-Jen Lin, and Bernhard Scholkopf in *A Tutorial on v-Support Vector Machines*, APPLIED STOCHASTIC MODELS IN BUSINESS AND INDUSTRY 21:111-136 (2005), which is incorporated herein by reference. Commonly, a factor of ½ is prepended to the objective function. This merely makes the derivatives easier to deal with, as in e.g., $f(x) = \frac{1}{2} x^2 \Rightarrow f'(x) = x$.

The above formulations assume that the data are feasible, i.e., that there is at least one w and b that correctly classifies all the data. This may not always be true, due to measurement error, or due to unsuitability of the linear classifier model. There is no clear definition of an "optimal" classifier when this is the case. Solutions redefining the "optimal" classifier may include the following:

1. A classifier which maximizes the margin. The margin in this case would be negative because not all the data points can correctly be classified, however, the margin still measures distance to the classifier line.
2. A classifier which correctly classifies all but k of the training data points, for some number k, and which has maximal margin for that subset of training data.
3. Some combination of suggested solutions 1 and 2. For example, a classifier which correctly classifies all but k of the training data, and for which the margins of the remaining k data points are not too bad.

Other approaches may also be devised which would define an "optimal" classifier for instances of infeasible data. Each of the different approaches, however, would be subject to different implementation schemes and may or may not be supported by theory, depending on the model used for the data.

The Chen, et al. article, for example, discusses two ways of dealing with infeasible data, or the "soft margin" problem, on v-SVMs. First, slack variables $\xi_i \geq 0$ are introduced to take up slack in each classification. Specifically, it is required:

$$(w^T x_i + b) y_i \geq 1 - \xi_i \forall i. \quad (8).$$

For those i which the classifier correctly classifies, $\xi_i$ equal zero. Because the slack variables could take up all errors and w can be any variable, minimization of $w^T w$ of equation (6) would not work. Thus, the objective function should also penalize large values of $\xi_i$. This has the effect of minimizing both the number of misclassified data points and the total magnitude by which they are misclassified, i.e., their distance from the classifier line. This leads to the "C-form" of the problem:

$$\min_{w,b,\xi:\xi \geq 0, (w^T x_i + b) y_i \geq 1 - \xi_i, \forall i} \|w\|_2^2 + C \sum_i \xi_i. \quad (9)$$

The sum $$\sum_i \xi_i$$

in the objective ensures that there are few nonzero $\xi_i$ in the objective helps ensure that there are few nonzero $\xi_i$, and that they are small in magnitude. The factor C controls the balance between how much $\|w\|_2^2$ is minimized and how much the sum of slack variables are minimized. The C must be chosen a priori, which may require some a priori knowledge about the data, or some statistical preprocessing and heuristics.

An alternative form is the "v-form," in which v controls a lower bound on the number of support vectors, and an upper bound on the number of misclassified data points. This is written as:

$$\min_{w,b,\xi,\rho:\rho > 0, \xi \geq 0, (w^T x_i + b) y_i \geq \rho - \xi_i, \forall i} \frac{1}{2} \|w\|_2^2 - v\rho + \frac{1}{m} \sum_i \xi_i. \quad (10)$$

Figure 6:
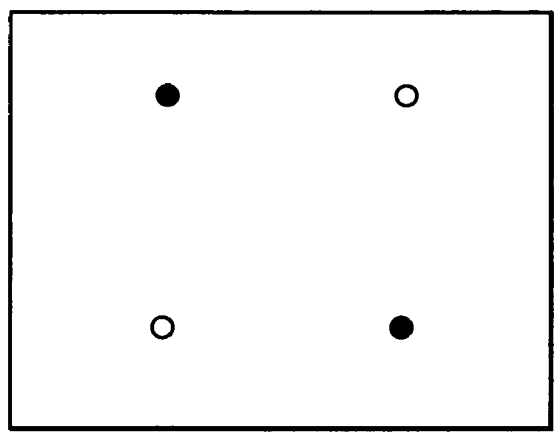
FIG. 6 illustrates a set of non-separable data points in accordance with an exemplary embodiment of the present invention.

Returning to the case of calibration data for which there exists a linear discriminator with positive margin, the data is called "separable." In other words, the data is separable if the data can be classified with a linear discriminator. FIG. 6 illustrates an example of non-separable calibration data. Specifically, there is no linear discriminator with a positive margin to rationally discriminate the data points that are solid and the data points that are open.

Figure 7:
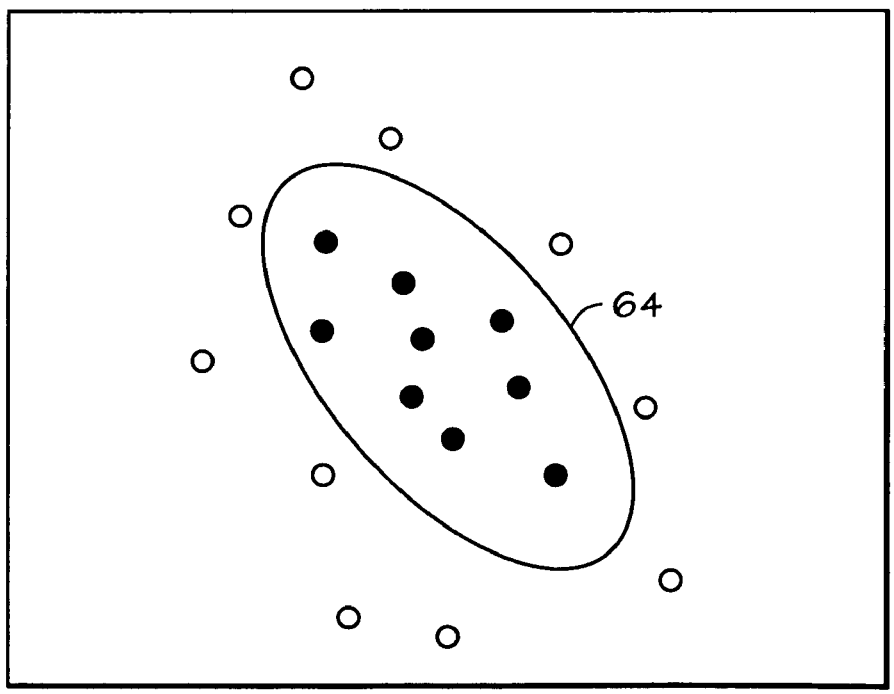
FIG. 7 illustrates classification of data points using a non-linear discriminator in accordance with an exemplary embodiment of the present invention.

Alternatively, FIG. 7 illustrates data which is separable by a nonlinear discriminator 64. To construct a nonlinear discriminator while retaining the theoretical grounding of linear discriminators, a linear discriminator with a nonlinear transform can be composed:

$$f(x) = \text{sign}(w^T \Phi(x) + b), \quad (11)$$

where $\Phi: \mathbb{R}^l \to \mathbb{R}^L$ is a nonlinear transform, and w is an L-vector.

An example is the transform $\Phi(x)=(\chi_1^2, \sqrt{2}\chi_1\chi_2, \chi_2^2)$, which carries points from $\mathbb{R}^2$ to $\mathbb{R}^3$. The hyperplane dividers in $\mathbb{R}^3$ correspond to ellipses in $\mathbb{R}^2$ under the inverse of this $\Phi$. The nonlinear discriminator 64, therefore, has a generally elliptical shape, encircling only the solid data points, and correctly classifies the data of FIG. 7. By setting $\Phi$ to the identity transform from $\mathbb{R}^l$ to $\mathbb{R}^L$, with L=l, the linear case is recovered. Since the transform $\Phi$ subsumes the linear case, it will be assumed for use in the following discussion regarding training a classifier.

Training a Classifier

With the calibration data (i.e., the training data vectors $x_i$ and their classifying signs $y_i$, as adjudged by an expert) and the transform $\Phi$, the task becomes finding the unit-length vector w and scalar b that maximize the margin $\epsilon$. A more thorough discussion of the optimization process is discussed in the articles by Smola and Sholkopf, which have been incorporated herein by reference. The optimization may be performed by commercially available software packages that accept the training data and variable parameters (kernel type and kernel parameters). The optimization may, however, utilize a large amount of computing power. Once the proper w and b are found, classification becomes rather simple using of the function $f$ defined in equation (11). The primal variable w and scalar b can be built into an oximetry system to classify data obtained by the oximeter.

As mentioned above, the technical details of how the maximization is performed are not important for describing the programming of the oximeter, a more detailed treatment of optimization, however, may be found in *Numerical Optimization*, by Jorge Nocedal and Stephen J. Wright, Springer Verlag New York, Inc. (1999), which is incorporated herein by reference. In the context of an SVM, the Lagrange dual form allows the implementation of the "Kernel Trick." A more detailed description of the Lagrange dual form may be found in the Chen et al. and Smola and Scholkopf articles which are incorporated herein by reference. Briefly, the kernel trick is the equivalent of transforming the data $$\{x_i\}_{i=1}^n,$$

and any vector x to be classified into some feature space by means of the transform $\Phi$, and then performing a linear classification in the featured space. Using the kernel trick, one can capture the advantage of linear classification in the feature space without heavy computational costs. Indeed, the function $\Phi$ need not be computed or even known to perform the maximization or to use the classifier in an oximetery system. This is because it can be shown that the optimal vector w is spanned by the transforms of the calibration data, i.e., $$w = \sum_i \alpha_i \Phi(x_i), \quad (12)$$

for some real numbers $x_i$ which have to be determined in the optimization. This can also be seen as the consequence of the Karush-Kuhn-Tucker necessary conditions on optimality or by considering the case where the set $\{\Phi(x_i)\}$ does not span $\mathbb{R}^L$. Any prospective w* not in the span of the $\Phi(x_i)$ can be projected into the span, resulting in a larger margin.

Under this choice of w, the separator function of equation 4 can be re-written as $$f(x) = \text{sign}\left(b + \sum_i \alpha_i \Phi(x_i)T\Phi(x)\right) = \text{sign}\left(b + \sum_i \alpha_i k(x_i, x)\right), \quad (13)$$

where the function $k(x, x')=\Phi(x)^T\Phi(x')$ is the kernel function. In the training and use of a support vector machine (SVM) via this "kernel trick," the use of the function $\Phi$ can be avoided. Instead, only the kernel function k is used. Commonly used kernels include the polynomial, the Gaussian, the sigmoidal, and the triangular kernel. The Chen et. al. and Smola and Scholkopf articles discuss several of these kernels in detail and reference can be made to those articles for additional information.

Moreover, theorems, such as Mercer's Theorem, assert that under certain conditions a given function k is the kernel function of some transform $\Phi$, without specifying the transform. The kernel trick, therefore, avoids the curse of dimensionality and linear classifiers in $\mathbb{R}^L$ can be reasoned for some large L without having to explicitly transform l-vectors into the space, providing a computational advantage. Once the factors $\alpha_i$ have been found, they can be used to compute the function $f$ as given in equation (13).

Programming the Oximeter

An oximeter may be programmed to execute the equation (13) using the calibration data and the variables $\alpha_i$. The computing use of the dual variables $\alpha_i$ and the kernel function provides significant computational savings over implementing a system using the primal variables $w_i$ and the transform function $\Phi$.

The oximeter may be configured to receive additional calibration data as it becomes available or, alternatively, the oximeter may be configured to add data from patients to the calibration data periodically. Specifically, the patient's data may be added to the calibration data when prompted by a physician, or, alternatively, according to a schedule. Additionally, the oximeter may be configured to accept a physician's override of a classification. For example, in the event the oximeter indicates a pathological condition and upon review by a physician no pathological condition exists, the physician may re-classify the patient's data and add the re-classified data to the calibration data. Thus, the oximeter can continuously increase its knowledge base in order to better classify patient data.

Figure 8:
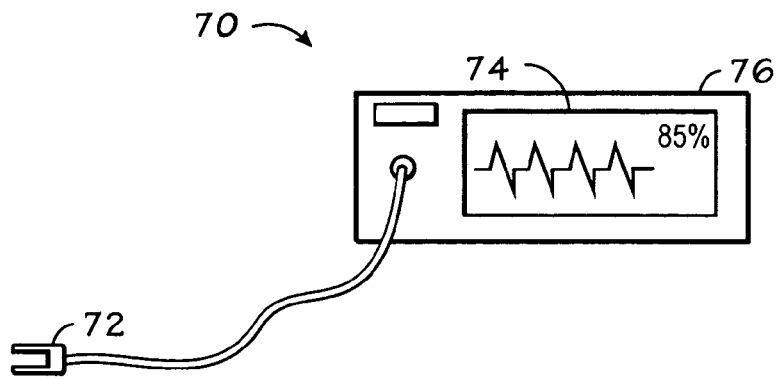
FIG. 8 illustrates a block diagram of an oximeter system in accordance with an exemplary embodiment of the present invention.

Referring to FIG. 8, a block diagram of an oximeter system 70 configured to classify trace data is illustrated in accordance with embodiments of the present invention. The oximeter system 70 includes a sensor 72 configured to couple electromagnetic radiation into a patient's tissue and detect electromagnetic radiation from the tissue. The detected electromagnetic radiation is directed to an oximeter 74. The oximeter 74 is configured to process the detected electromagnetic radiation signals to determine various physiological parameters, such as a patient's SpO$_2$ level, for example. Additionally, the oximeter 74 may have a display 76 configured to output the various physiological parameters that have been calculated. Specifically, the display 76 may show the percent saturation of hemoglobin (SpO$_2$) and a saturation trace (SpO$_2$ vs. time), among other things.

The oximeter 74 is programmed to use the SVM described above to classify saturation traces into two categories: Normal and Not Normal. The Normal category can be represented by a +1 and the Not Normal category can be represented by a −1.

As described above, the Not Normal, or −1, state indicates the potential of an underlying pathological problem that may need attention. Thus, when the classifier of the oximeter 74 determines a Not Normal condition, an alarm can be initiated.

The alarm can be visual, audible, or both. A visual alarm may be one that appears on the display 76 of the oximeter 74. For example, a graphical alarm symbol may appear on the display 76 or the display may flash on and off to indicate that a pathological condition has been detected. Alternatively, a light, such as a red colored LED light on the face of the oximeter 74, may turn on or flash on and off. The audible alarm should have a pitch and volume such that attention can be called to the patient. Additionally, the audible alarm can vary in pitch and/or volume.

Figure 9:
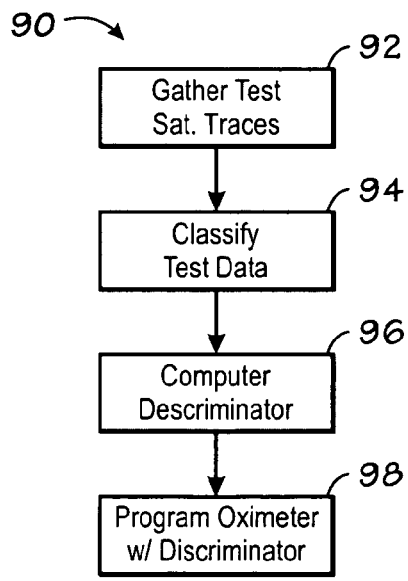
FIG. 9 is a flow chart illustrating a technique for training an oximeter for classification of saturation traces in accordance with an exemplary embodiment of the present invention.

A flow chart illustrating a technique 90 for programming the oximeter 74 in accordance with an exemplary embodiment of the present invention is shown in FIG. 9. The technique 90 begins by gathering training saturation data, as indicated at block 92. Data may be gathered from multiple patients over a period of a few hours or days such that a good representative data set may be produced. An expert classifies the data as being Normal or Not Normal as indicated at block 94. Specifically, the data is presented to an expert who is trained in evaluating saturation trace trends and is capable of recognizing problematic traces simply by observing the traces. The traces may be representative of measurements taken over a matter of a few seconds, a few minutes, or even tens of minutes, as the trends for particular conditions may only emerge over longer periods. For such patterns or periods, the IIR parameters (or the saturation trace sampling rate) may be tuned to reflect the proper timescale.

The classified data is provided to a computing device which performs a statistical analysis of the Normal and Pathological trace trends, as indicated at block 96. From this statistical analysis, an SVM may be created which is capable of classifying other saturation traces. The SVM is programmed into the oximeter 74, as indicated at block 98. The kernel trick described in detail above affords significant computing savings to the oximeter system, in that it allows for classification of the data without having to transform l-vectors into the feature space. Additionally, time savings may be gained during the training process. The number of support vectors, $x_i$, which correspond to nonzero $\alpha_i$ can be reduced if the classifier margin is "softened." In other words, a less accurate classifier could be constructed which requires less memory providing cost savings. However, it should recognized that, generally, l different $x_i$ different support vectors of length l will be programmed into the oximeter. Thus, the memory requirements are on the order of l squared. The smaller memory may, therefore, limit the number of statistics computed from the saturation trace.

Using the Oximeter

Figure 10:
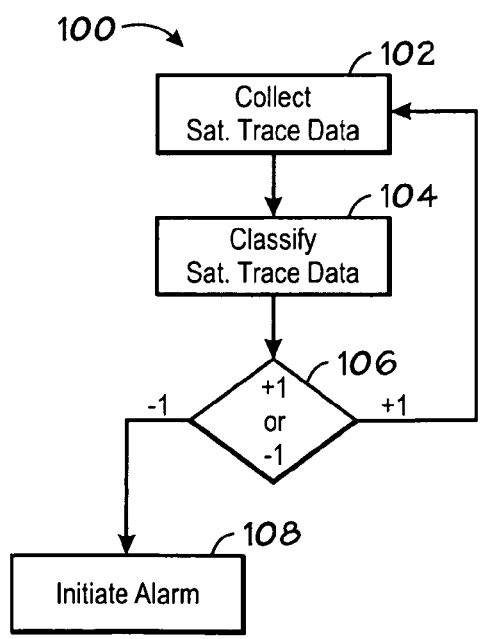
FIG. 10 is a flow chart illustrating a technique for classification of saturation traces in accordance with an exemplary embodiment of the present invention.

Once the oximeter 74 is programmed with the SVM, it may be used to determine the presence of a pathological condition of a patient. FIG. 10 is a flow-chart detailing the technique 100 used by the oximeter 74 to detect the presence of a pathological condition. The oximeter 74 begins by collecting saturation trace data, as indicated by block 102. Specifically, for example, the sensor 72 of the oximetry system 70 of FIG. 8 transmits electromagnetic radiation into the blood perfused tissue of a patient. The sensor 72 detects the transmitted electromagnetic radiation after it has passed through the blood perfused tissue and provides the detected signal to the oximeter 74.

After the signal is passed to the oximeter 74, the oximeter 74 processes the signal to determine various physiological parameters, as discussed earlier. Concurrently, the oximeter 74 classifies the data as being indicative of normal or pathological conditions, as shown by block 104. Specifically, the data is classified to have either a +1 or a −1 sign, representative of a normal or pathological state, respectively, as indicated by the decision block 106. In the even that a 1 is obtained, the oximeter 74 continues collecting data and the technique 100 is repeated starting at block 102.

If, however, a −1 is obtained, the oximeter 74 may initiate an alarm, as indicated at block 108. The alarm may implement visual and/or audible features to draw the attention of a caregiver to the fact that a pathological condition has been detected. Once a pathological condition has been detected, and the alarm has been initiated, the alarm may be configured to continue until the alarm has been reset. A button, or other means may be provided for resetting the alarm. Therefore, even if subsequent data does not indicate a pathological condition, the alarm may continue so that a caregiver can be notified of such an occurrence.

In addition to the detection of airway instability, there are a number of other uses for nonlinear classifiers in oximetry, as set forth above. Additionally, for example, the classifier can be used for detecting a sensor-off condition, weakened heart capacity or high blood pressure. The sensor-off condition is currently performed by a neural network. Kernel methods, however, may be preferable to neural networks because there are a wider variety of available kernel functions and a more solid theoretical basis.

The SVM for detecting a sensor-off condition may be trained as described above with regards to the classifier for a pathological condition. The sensor-off classifier may be implemented in conjunction with a pathological condition classifier. Specifically, an oximeter programmed to detect a sensor-off condition may first apply the sensor-off classifier to measured data to determine if the sensor is on the patient. If it is determined that the sensor is on the patient, then data the classifier for indicating a normal or pathological condition may be implemented. If however, it is determined that the sensor is not on the patient, then there is no need to run the classifier for the pathological condition.

Implementation of the present techniques to determine additional or alternative pathologies requires independent training and programming of the support vector machine. Specifically, a trained expert may classify trace data or other data produced by the oximeter as indicating or not indicating the particular condition. Statistical data is then generated and used to determine vectors used to define regions indicative of the pathological condition, as described above. The oximeter is then programmed with the SVM and calibration data, and configured to indicate the detection of the particular condition.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of manufacturing a pulse oximeter configured to classify patient data comprising:

generating statistics of interest representing sample data, wherein the sample data comprises oxygen saturation traces classified as either pathological or normal using human expertise, and the statistics of interest comprise at least one of linearity or infinite impulse response least squares regression of saturation variance of the sample data;

composing a linear discriminator having a non-linear transform that accepts as input the statistics of interest; and programming a pulse oximeter to compute the linear discriminator using a kernel function, wherein the pulse oximeter is configured to use the linear discriminator to classify measured parameters of the patient data as indicating a normal or pathological condition and to communicate the classification to a user.

2. The method of claim 1, comprising computing a unit-length vector w and scalar b that maximize a margin $\epsilon$ defined as $$\epsilon = \min_i \frac{wTx_i + b}{\|w\|_2} Y_i;$$

wherein $x_i$ is sample data, and $Y_i$ is a classifier signal 1 or −1.

3. The method of claim 1 comprising finding an optimal classifier by computing $$\min_{w,b:(w^T x_i + b) y_i \geq 1} \|w\|_2^2 = w^T w,$$

wherein w is a vector and b is a scalar.

4. The method of claim 1, comprising defining an optimal classifier to account for infeasible data.

5. The method of claim 1, wherein the saturation traces are obtained from a plurality of people.

6. The method of claim 1, wherein the kernel function comprises $k(x, x') = \Phi(x)^T \Phi(x')$ and the linear discriminator comprises:

$$f(x) = \operatorname{sign}\left(b + \sum_i \alpha_i \Phi(x_i) T \Phi(x)\right) = \operatorname{sign}\left(b + \sum_i \alpha_i k(x_i, x)\right),$$

wherein 60 $_i$ is an optimized dual variable, $x_i$ is sample data, and x is the measured parameter.

7. The method of claim 1, comprising providing an alarm to operate in conjunction with the classifier.

8. The method of claim 7, wherein providing the alarm comprises providing a visual alarm.

9. The method of claim 7, wherein providing the alarm comprises providing an audible alarm.

10. The method of claim 7, wherein providing the alarm comprises providing an audible alarm and a visual alarm.

11. The method of claim 1, comprising storing patient data with classifying signs and updating the linear discriminator using the stored patient data and classifying signs.

12. The method of claim 1, comprising configuring the pulse oximeter to allow for a user to override a classification of the patient data and add the patient data corresponding to the classification to the sample data.

13. A method for detecting a pathological condition comprising:

obtaining percent oxygen saturation data from a patient using a pulse oximeter; and classifying the percent oxygen saturation data using a kernel based classifier programmed into the pulse oximeter, the kernel based classifier being trained on statistics of interest representing sample data categorized by a trained expert, the statistics of interest comprising at least one of linearity or infinite impulse response least squares regression of saturation variance of the sample data, and the kernel based classifier being configured to categorize the percent oxygen saturation data as indicating a normal state or a pathological state; and adding the percent oxygen saturation data to the sample data used for training the kernel based classifier periodically with the pulse oximeter.

14. The method of claim 13, wherein the kernel based classifier implements a linear discriminator comprising:

$$f(x) = \operatorname{sign}\left(b + \sum_i \alpha_i \Phi(x_i) T \Phi(x)\right) = \operatorname{sign}\left(b + \sum_i \alpha_i k(x_i, x)\right),$$

wherein b is a scalar, $\alpha$hd i is an optimized dual variable, $x_i$ is sample data, and x is the measured data.

15. The method of claim 13, wherein the detection of a pathological condition initiates an alarm.

16. The method of claim 15, wherein the alarm comprises an audible alarm.

17. The method of claim 15, wherein the alarm comprises a visual alarm.

18. The method of claim 17, wherein the alarm comprises an audible alarm.

19. The method of claim 13, wherein the classifier is configured to determine an apneaic pathology.

20. The method of claim 13, wherein the classifier is configured to determine an airway instability pathology.

21. The method of claim 13, wherein the classifier is configured to determine a respiratory distress pathology.

22. An oximeter system configured to detect a pathological condition comprising:

a sensor unit configured to generate a signal representative of detected electromagnetic radiation that has been transmitted into blood perfused tissue; and an oximeter unit configured to determine percent saturation of hemoglobin data based on the signal and configured to classify the percent saturation of hemoglobin data as being normal or pathological according to a kernel based classifier, wherein the kernel based classifier is trained using statistics of interest representing sample data that has been classified by a human expert and statistically analyzed, the statistics of interest comprising at least one of linearity or infinite impulse response least squares regression of saturation variance of the sample data, and wherein the oximeter unit is configured to add the percent saturation of hemoglobin data to the sample data used for training the kernel based classifier periodically.

23. The oximeter system of claim 22 comprising an alarm configured to actuate if the data is classified as pathological.

24. The oximeter system of claim 23, wherein the alarm comprises an audible alarm.

25. The oximeter system of claim 23, wherein the alarm comprises a visual alarm.

26. The oximeter system of claim 23, wherein the alarm comprises a visual alarm configured to activate in conjunction with an audible alarm.

27. The oximeter system of claim 22, wherein the oximeter unit is configured to allow a user to override a classification made by the oximeter unit and store the re-classified data with sample data used to train the kernel based classifier.

28. The oximeter system of claim 22, wherein the classifier is configured to determine an apneaic pathology.

29. The oximeter system of claim 22, wherein the classifier is configured to determine an airway instability pathology.

30. The oximeter system of claim 22, wherein the classifier is configured to determine a respiratory distress pathology.

31. The oximeter system of claim 22, wherein the classifier is configured to determine a sensor-off condition.

* * * * *